United States Patent

Krämer et al.

[11] Patent Number: 6,028,089
[45] Date of Patent: Feb. 22, 2000

[54] PHENYLTHIO-OXAZOLINE COMPOUNDS AND THEIR USE AS PESTICIDES

[75] Inventors: Wolfgang Krämer, Burscheid; Ulrike Wachendorff-Neumann, Neuwied; Christoph Erdelen, Leichlingen; Andreas Turberg, Erkrath; Norbert Mencke, Leverkusen, all of Germany

[73] Assignee: Bayer Aktiengesellschaft, Leverkusen, Germany

[21] Appl. No.: 09/030,489

[22] Filed: Feb. 25, 1998

Related U.S. Application Data

[63] Continuation of application No. 08/669,523, filed as application No. PCT/EP95/00020, Jan. 4, 1995, abandoned.

[30] Foreign Application Priority Data

Jan. 17, 1994 [DE] Germany ............................ 44 01 101

[51] Int. Cl.[7] ........................ A01N 43/76; C07D 263/14; C07D 401/04
[52] U.S. Cl. ........................ 514/374; 548/237; 548/238; 548/239
[58] Field of Search .................... 548/237, 238, 548/239; 514/374

[56] References Cited

U.S. PATENT DOCUMENTS

| | | | |
|---|---|---|---|
| 3,901,906 | 8/1975 | Kozlik . | |
| 5,411,979 | 5/1995 | Hirose et al. | 514/374 |
| 5,556,867 | 9/1996 | Hirose et al. | 514/374 |
| 5,639,771 | 6/1997 | Obata et al. | 548/237 |

FOREIGN PATENT DOCUMENTS

| | | |
|---|---|---|
| 0 168 813 | 1/1986 | European Pat. Off. . |
| 0 345 775 | 12/1989 | European Pat. Off. . |
| 0 553 623 | 8/1993 | European Pat. Off. . |

OTHER PUBLICATIONS

Mencke et al. Chem. Abstract. vol. 126, Entry 117963 Abstracting DE 1 95 20 936 (1996).

Lahm et al. Chem. Abstract vol. 23 Entry 198780 (1995).

*Primary Examiner*—Mukund J. Shah
*Assistant Examiner*—Brenda Coleman
*Attorney, Agent, or Firm*—Sprung Kramer Schaefer & Briscoe

[57] ABSTRACT

The invention relates to new phenylthio-oxazoline derivatives of the formula (I)

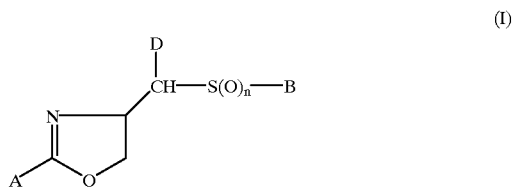

in which
A represents optionally substituted phenyl;
B represents optionally substituted phenyl;
D represents hydrogen or alkyl; and
n represents 0, 1 or 2;
to a plurality of processes for their preparation, and to their use as pesticides.

11 Claims, No Drawings

PHENYLTHIO-OXAZOLINE COMPOUNDS AND THEIR USE AS PESTICIDES

This application is a continuation of Ser. No. 08/669,523 filed Jul. 10, 1996, now abandoned, which is a § 371 application of PCT/EP95/00020, filed Jan. 4, 1995.

The invention relates to new phenylthio-oxazoline derivatives, to a plurality of processes for their preparation, and to their use for combating animal pests.

It is already known that certain oxazoline derivatives have insecticidal and acaricidal properties (cf., for example, EP-A 0 553 623). However, the activity of these prior-art compounds is not entirely satisfactory in all fields of application, in particular when low application rates and concentrations are used.

The new phenylthio-oxazoline derivatives of the formula (I)

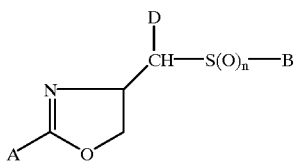

in which
A represents optionally substituted phenyl;
B represents optionally substituted phenyl;
D represents hydrogen or alkyl; and
n represents 0, 1 or 2;
have now been found.

Furthermore, it has been found that phenylthio-oxazoline derivatives of the formula (I) are obtained by a process which comprises
a) reacting aminoalcohols of the formula (II)

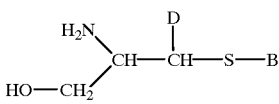

in which
B and D have the abovementioned meanings
with a carboxylic acid of the formula (III)

   (III)

in which
A has the abovementioned meaning
and with a dehydrating agent, if appropriate in the presence of a diluent;
or
b) reacting amidoalcohols of the formula (IV)

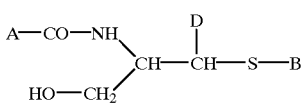

in which
A, B and D have the abovementioned meanings with a dehydrating agent, if appropriate in the presence of a diluent;
or
c) reacting amide derivatives of the formula (V)

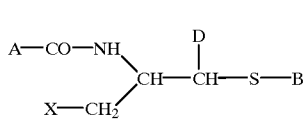

in which
A, B and D have the abovementioned meanings and
X represents a leaving group, such as halogen, alkylsulfonyloxy or arylsulfonyloxy,
with a base, if appropriate in the presence of a diluent;
or
d) reacting oxazolines of the formula (VI)

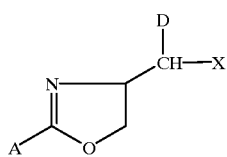

in which
A, D and X have the abovementioned meanings with thiophenols of the formula (VII)

   (VII)

in which
B has the abovementioned meaning
in the presence of a base and if appropriate in the presence of a diluent;
and, if appropriate
e) reacting the phenylthio-oxazoline derivatives of the formula (Ia)

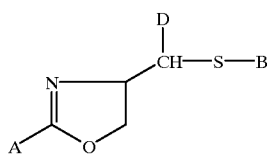

in which
A, B and D have the abovementioned meanings and
which can be obtained by processes (a) to (d)
with an oxidant, if appropriate in the presence of a diluent and if appropriate in the presence of a reaction auxiliary.

Furthermore, it has been found that diphenyloxazoline derivatives of the formula (I) are highly suitable for combating animal pests. In particular, they are distinguished by a powerful activity against arthropods and nematodes.

Surprisingly, the diphenyloxazoline derivatives of the formula (I) according to the invention show a considerably better activity against animal pests than the prior art compounds of the most similar constitution.

Formula (I) provides a general definition of the compounds according to the invention.

Preferred substituents or ranges of the radicals listed in the formulae mentioned hereinabove and hereinbelow will be illustrated in the following text.

A preferably represents phenyl which is optionally monosubstituted to pentasubstituted by identical or different substituents from the series consisting of halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy or $C_1$–$C_6$-halogenoalkylthio;

B preferably represents phenyl which is optionally monosubstituted to tetrasubstituted by identical or different substituents from the series consisting of halogen, $C_1$–$C_{18}$-alkyl, cyano, $C_1$–$C_8$-alkoxy-$C_1$–$C_8$-alkyl, $C_1$–$C_8$-halogenoalkoxy, $C_1$–$C_4$-halogenoalkyl, $C_1$–$C_{18}$-alkoxy which is optionally interrupted by a further 1–3 oxygen atoms, $C_1$–$C_{18}$-alkylthio, $C_1$–$C_8$-halogenoalkylthio, 3,4-difluoromethylenedioxo, 3,4-tetrafluoroethylenedioxo, benzyliminooxymethyl which is optionally substituted by $C_1$–$C_4$-alkyl, $C_3$–$C_6$-cycloalkyl and/or halogen, cyclohexyl or cyclohexyloxy, which is optionally substituted by $C_1$–$C_6$-alkyl, $C_1$–$C_6$-alkoxy, cyclohexyl or phenyl;

pyridyloxy which is optionally monosubstituted or disubstituted by identical or different substituents from the series consisting of halogen, $C_1$–$C_4$-alkyl or $C_1$–$C_4$-halogenoalkyl;

phenyl, phenylcarbonyl, benzyl, phenoxy, phenylthio, benzyloxy, benzyloxycarbonyl or benzylthio, each of which is optionally monosubstituted to trisubstituted by identical or different substituents from the series consisting of $C_1$–$C_{12}$-alkyl, halogen, $C_1$–$C_4$-halogenoalkyl, $C_1$–$C_6$-alkoxy, $C_1$–$C_6$-halogenoalkoxy, $C_1$–$C_6$-alkoxy-$C_1$–$C_6$-alkyl, $C_1$–$C_6$-alkoxyethyleneoxy, $C_1$–$C_6$-alkylthio and/or $C_1$–$C_6$-halogenoalkylthio;

$C_1$–$C_{12}$-alkyl-carbonyl, $C_1$–$C_{12}$-alkoxy-carbonyl, $C_5$–$C_7$-cycloalkyloxy-carbonyl which is optionally substituted by $C_1$–$C_6$-alkyl and/or $C_1$–$C_6$-alkoxy;

$C_5$–$C_7$-cycloalkyl-$C_1$–$C_6$-alkyloxy-carbonyl which is optionally substituted in the cycloalkyl moiety by $C_1$–$C_6$-alkyl and/or $C_1$–$C_6$-alkoxy; and the group —CO—$NY^1Y^2$ in which
$Y^1$ and $Y^2$ are identical or different and have the following meanings:
hydrogen,
$C_1$–$C_6$-alkyl,
$C_5$–$C_7$-cycloalkyl which is optionally substituted by $C_1$–$C_6$-alkyl and/or $C_1$–$C_6$-alkoxy, and
benzyl which is optionally substituted by the above-mentioned benzyl substituents.

D preferably represents hydrogen or methyl;

n preferably represents 0, 1 or 2.

A particularly preferably represents phenyl which is optionally monosubstituted to pentasubstituted by identical or different substituents from the series consisting of F, Cl, Br, $C_1$–$C_3$-alkyl, $C_1$–$C_3$-alkoxy, $C_1$–$C_3$-alkylthio, $C_1$–$C_2$-alkyl which is monosubstituted to pentasubstituted by identical or different substituents from the series consisting of F and Cl, $C_1$–$C_4$-alkoxy which is monosubstituted to pentasubstituted by identical or different substituents from the series consisting of F and Cl, $SCF_3$ or $SCHF_2$;

B particularly preferably represents phenyl which is optionally monosubstituted to tetrasubstituted by identical or different substituents from the series consisting of F, Cl, Br, $C_1$–$C_{18}$-alkyl, cyano, $C_1$–$C_6$-alkoxy-$C_1$–$C_8$-alkyl, $C_1$–$C_8$-alkoxy which is monosubstituted to hexasubstituted by identical or different substituents from the series consisting of F and Cl, $C_1$–$C_2$-alkyl which is monosubstituted to pentasubstituted by identical or different substituents from the series consisting of F and/or Cl, $C_1$–$C_{18}$-alkoxy and —$(OC_2H_4)_{1-3}$—O—$C_1$–$C_6$-alkyl, $C_1$–$C_{12}$-alkylthio, $C_1$–$C_8$-alkylthio which is monosubstituted to hexasubstituted by identical or different substituents from the series consisting of F and Cl, 3,4-difluoromethylenedioxo, 3,4-tetrafluoroethylenedioxo, the groups

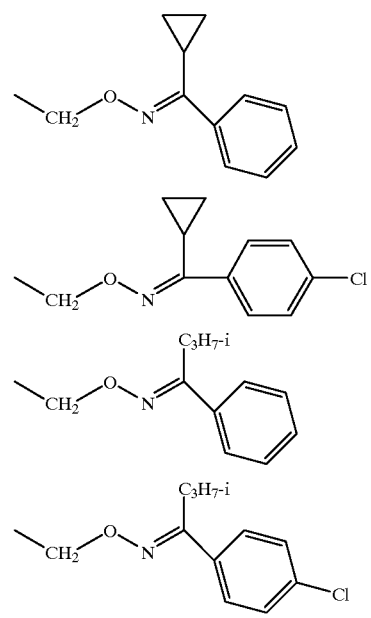

cyclohexyl or cyclohexyloxy, each of which is optionally substituted by $C_1$–$C_4$-alkyl, $C_1$–$C_4$-alkoxy, cyclohexyl or phenyl;

pyridyloxy which is optionally monosubstituted or disubstituted by identical or different substituents from the series consisting of F, Cl or $CF_3$, phenyl, phenylcarbonyl, benzyl, phenoxy, phenylthio, benzylthio, benzyloxy, benzyloxycarbonyl or benzylthio, each of which is optionally monosubstituted to trisubstituted by identical or different substituents from the series consisting of $C_1$–$C_{12}$-alkyl, F, Cl, Br, $CF_3$, $C_1$–$C_4$-alkoxy, $C_1$–$C_4$-alkoxy which is monosubstituted to hexasubstituted by identical or different substituents from the series consisting of F and Cl, $C_1$–$C_4$-alkoxy-$C_1$–$C_4$-alkyl, $C_1$–$C_4$-alkoxyethyleneoxy, $C_1$–$C_4$-alkylthio and $C_1$–$C_4$-alkylthio which is monosubstituted to hexasubstituted by identical or different substituents from the series consisting of F and Cl;

$C_1$–$C_{12}$-alkyl-carbonyl, $C_1$–$C_{12}$-alkoxy-carbonyl, $C_5$–$C_7$-cycloalkyloxy-carbonyl which is optionally substituted by $C_1$–$C_6$-alkyl and/or $C_1$–$C_6$-alkoxy;

$C_5$–$C_7$-cycloalkyl-$C_1$–$C_6$-alkyloxy-carbonyl which is optionally substituted in the cycloalkyl moiety by $C_1$–$C_6$-alkyl and/or $C_1$–$C_6$-alkoxy; and the group —CO—NY$^1$Y$^2$ in which $Y^1$ and $Y^2$ are identical or different and have the following meanings:

hydrogen, $C_1$–$C_6$-alkyl, $C_5$–$C_7$-cycloalkyl which is optionally substituted by $C_1$–$C_6$-alkyl and/or $C_1$–$C_6$-alkoxy, and also benzyl which is optionally substituted by the above-mentioned benzyl substituents.

D particularly preferably represents hydrogen or methyl;

n particularly preferably represents 0, 1 or 2.

The following radicals may be mentioned by way of example for the substituent A:

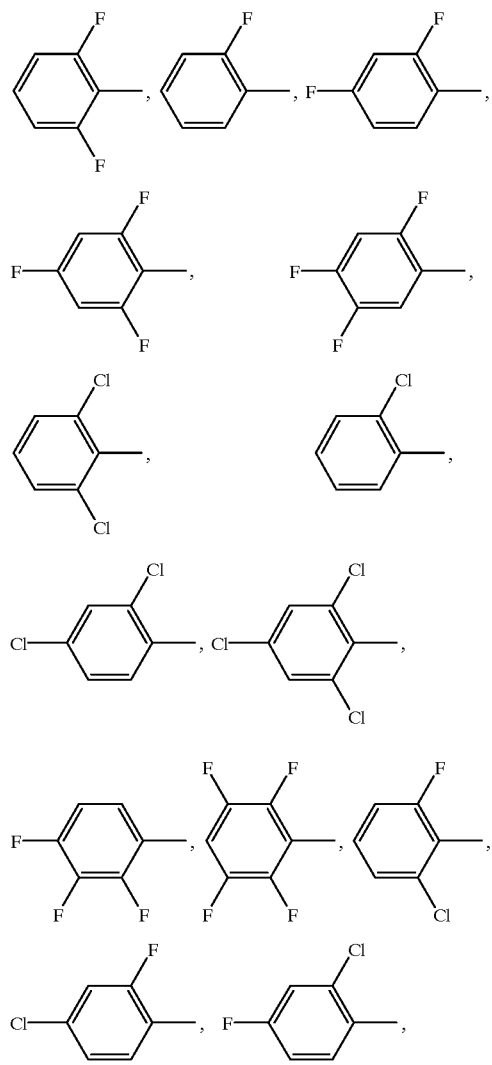

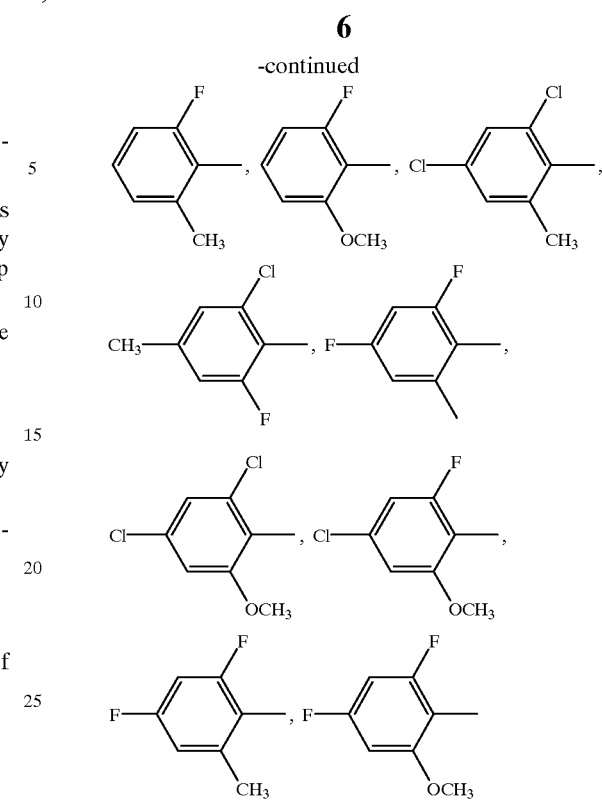

The following radicals may be mentioned by way of example for the substituent B:

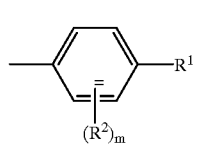

$R^1$ = as in Table 1
$(R^2)_m$ = as in Table 2

TABLE 1

| $R^1$ |
|---|
| Cl |
| F |
| —$C_4H_9$-t |
| —$C_6H_{13}$-n |
| —$C_{12}H_{25}$-n |
| —$C_{10}H_{21}$-n |
| —$C_8H_{17}$-n |
| —$C_9H_{19}$-n |
| $CF_3$ |
| —$CF_2CHF_2$ |
| —$OC_6H_{13}$-n |
| —$OC_8H_{17}$-n |
| —$OC_{12}H_{25}$-n |
| —$OCF_3$ |
| —$OCF_2CHF_2$ |
| —$OCH_2CF_3$ |
| —$OCF_2CHFCH_3$ |
| —CO—$C_4H_9$-i |
| —$OCF_2CHFCF_3$ |
| —$CH_2CH_2$—O—$C_2H_5$ |
| —$CH_2CH_2$—O—$C_4H_9$-n |
| —$CH_2CH_2$—O—$C_6H_{13}$-n |

TABLE 1-continued

| R¹ |
|---|
| —CH₂—O—N=C(cyclopropyl)(4-Cl-C₆H₄) |
| —SC₄H₉-n |
| —SC₆H₁₃-n |
| —SC₈H₁₇-n |
| —SC₁₂H₂₅-n |
| —SCF₃ |
| —SCF₂CHF₂ |
| —SCF₂CHFCH₃ |
| —CO—CH₃ |
| cyclohexyl |
| 4-t-C₄H₉-cyclohexyl |
| —O-cyclohexyl |
| —O-(4-t-C₄H₉-C₆H₄) |
| —C₆H₅ |
| —(4-Cl-C₆H₄) |
| —(4-Br-C₆H₄) |
| —(2,4-Cl₂-C₆H₃) |
| —(3,5-Cl₂-C₆H₃) |

TABLE 1-continued

| R₁ |
|---|
| —(4-Cl-2-CH₃-5-CH₃O-C₆H₃) (2-methyl-5-methoxy-4-chlorophenyl) |
| —C(O)—(4-Cl-C₆H₄) |
| —C(O)—(4-OCF₃-C₆H₄) |
| —(4-n-C₃H₇-C₆H₄) |
| —C(O)—(4-CF₃-C₆H₄) |
| —(4-n-C₄H₉-C₆H₄) |
| —(4-i-C₄H₉-C₆H₄) |
| —(4-s-C₄H₉-C₆H₄) |
| —(3-Cl-4-CH₃-C₆H₃) |
| —(3-Cl-4-n-C₃H₇-C₆H₃) |
| —(4-OC₂H₅-C₆H₄) |
| —(4-CF₃-C₆H₄) |

TABLE 1-continued
| R1 |
|---|
| 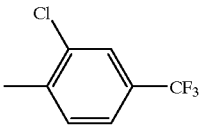 |
| 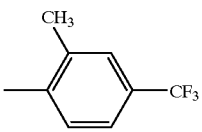 |
| 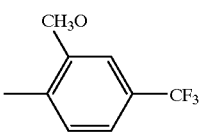 |
| 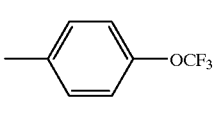 |
| 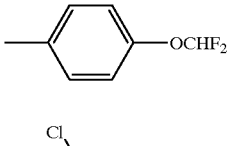 |
| 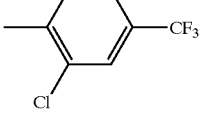 |
| 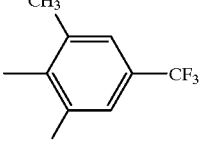 |
| 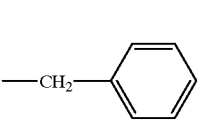 |
| 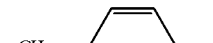 |
| 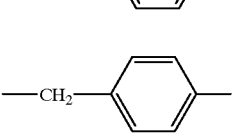 |
| 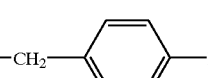 |
| 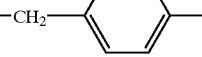 |
TABLE 1-continued
| R$^1$ |
|---|
| 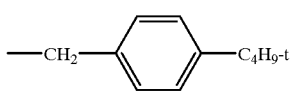 |
| 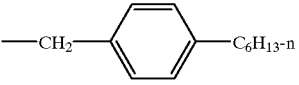 |
| 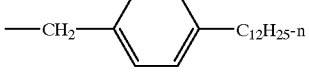 |
| 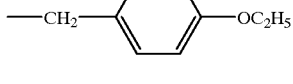 |
| 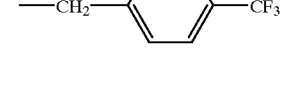 |
| 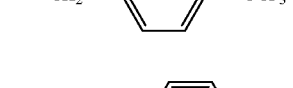 |
| 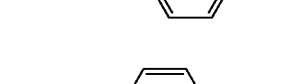 |
| 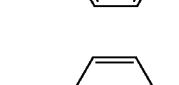 |
|  |
| 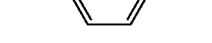 |
|  |
| 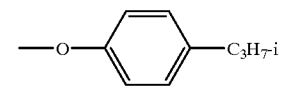 |
| 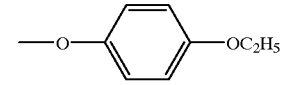 |

TABLE 1-continued

R¹

- —O—C₆H₃(2-CH₃)(4-OCH₃)
- —O—C₆H₃(2-Cl)(4-OC₂H₅)
- —O—C₆H₃(2-Cl)(4-OCH₃)
- —O—C₆H₃(3-CH₃)(4-Cl)
- —O—C₆H₂(2,6-Cl₂)(4-OCH₃)
- —O—C₆H₄(4-CH₂CH₂OC₂H₅)
- —O—C₆H₄(4-CF₃)
- —O—C₆H₃(3-CH₃)(4-CF₃)
- —O—C₆H₃(2-OCH₃)(4-CF₃)
- —O—C₆H₃(2-Cl)(4-CF₃)
- —O—C₆H₃(2-CH₃)(4-CF₃)
- —O—C₆H₄(4-OCF₃)
- —O—C₆H₄(4-OCHF₂)
- —O—C₆H₄(4-OCH₂CF₃)
- —O—C₆H₄(4-OCF₂CHF₂)
- —O—C₆H₄(4-OCF₂CHClF)
- —O—C₆H₄(4-OCF₂CHFCF₃)
- —CO—C₆H₅
- —O—C₆H₂(2,6-Cl₂)(4-CF₃)
- —O—C₆H₂(2,6-(CH₃)₂)(4-CF₃)
- —O—C₆H₂(2,6-Cl₂)(4-OCH₃)

TABLE 1-continued
R¹
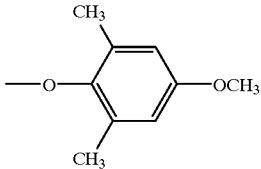
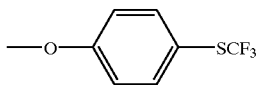
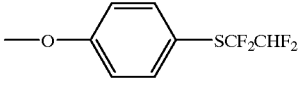
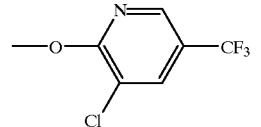
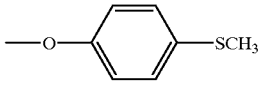
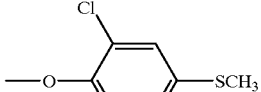
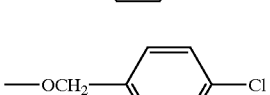
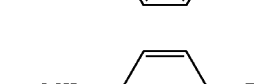
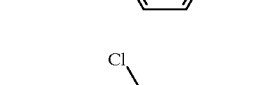
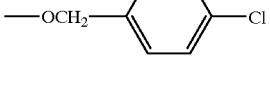
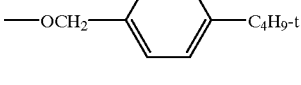
TABLE 1-continued
R¹
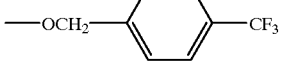
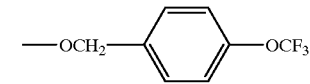
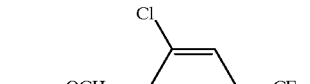
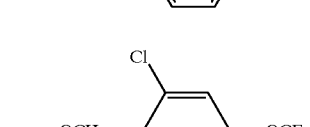
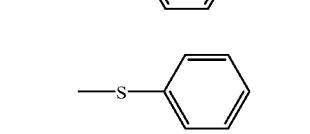
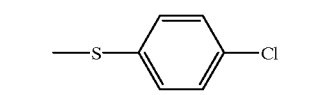
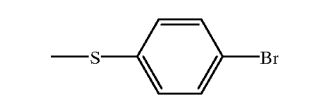
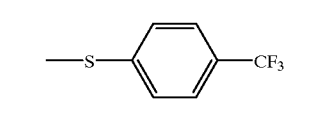
H
TABLE 2
$(R^2)_m$
—CO—O—$C_4H_9$-t
—CN
H
2-Cl
2-F
3-Cl
2,6-$Cl_2$
3,5-$Cl_2$
3,5-$F_2$
2,5-$Cl_2$
3,5-$Cl_2$; 2-F
2,3-$F_2$
2,5-$F_2$
2,3,5,6-$Cl_4$
3-$CF_3$
—CO—NH—$C_4H_9$-t
2-$CH_3$
2-$OCH_3$
2-$Cl_2$
2,6-$OC_2H_5$

TABLE 2-continued

| $(R^2)_m$ |
|---|
| 3-CH$_3$ |
| 3,5-OCH$_3$ |
| 3-OC$_6$H$_5$ |
| together with R$^1$ represents |
| 3,4-OCF$_2$O— |
| 3,4-OCF$_2$CF$_2$O |
| 2-Cl; 3-CF$_3$ |
| 2-Cl; 5-CF$_3$ |

The following examples of the compounds of the formula (Ib) according to the invention may be mentioned individually:

(Ib)

| A | R$^1$ | $(R^2)_m$ |
|---|---|---|
| 2,6-difluorophenyl | Cl | 2-Cl, 3-CF$_3$ |
| 2,6-difluorophenyl | —CO—C$_6$H$_5$ | — |
| 2,6-difluorophenyl | —CO—OC(CH$_3$)$_3$ | 2-CH$_3$ |
| 2,6-difluorophenyl | —C(CH$_3$)$_3$ | — |
| 2,6-difluorophenyl | Cl | 2-Cl, 5-CF$_3$ |

-continued (Ib)

[Structure: 2-A-substituted oxazoline with –CH₂–S–phenyl(R¹)(R²)ₘ group]

| A | R¹ | (R²)ₘ |
|---|----|-------|
| 2,6-difluorophenyl | —CO—NH—C(CH₃)₃ | — |
| 2,6-difluorophenyl | —CO—OC₄H₉-i | — |
| 2,6-difluorophenyl | —COCH₃ | 2-Cl |
| 2,6-difluorophenyl | —OCF₂—CHF—CF₃ | 2,5-Cl₂ |
| 2-fluorophenyl | —OCF₂—CHF—CF₃ | 2,5-Cl₂ |
| 2-fluorophenyl | —O—(4-chlorophenyl) | 3,5-Cl₂ |
| 2-fluorophenyl | —O—(2-chloro-4-trifluoromethylphenyl) | 2-F |

-continued
| | (Ib) |
|---|---|
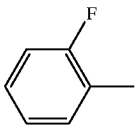
| A | R¹ | (R²)ₘ |
|---|---|---|
| 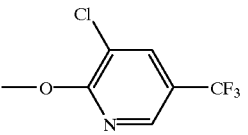 | 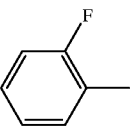 | 3,5-Cl₂ |
| 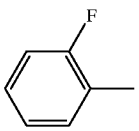 | O—CF₂—CHF₂ | 3,5-Cl₂ |
| 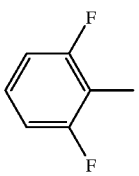 | F | 2-F; 3,5-Cl₂ |
| 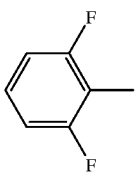 | F | 2-F; 3,5-Cl₂ |
| 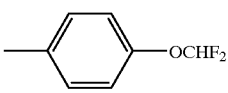 | 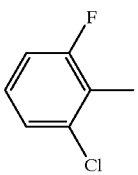 | — |
| 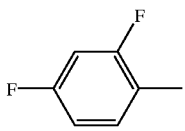 | CF₃ | 2,3-F₂ |
| | CF₃ | 2,3-F₂ |

-continued

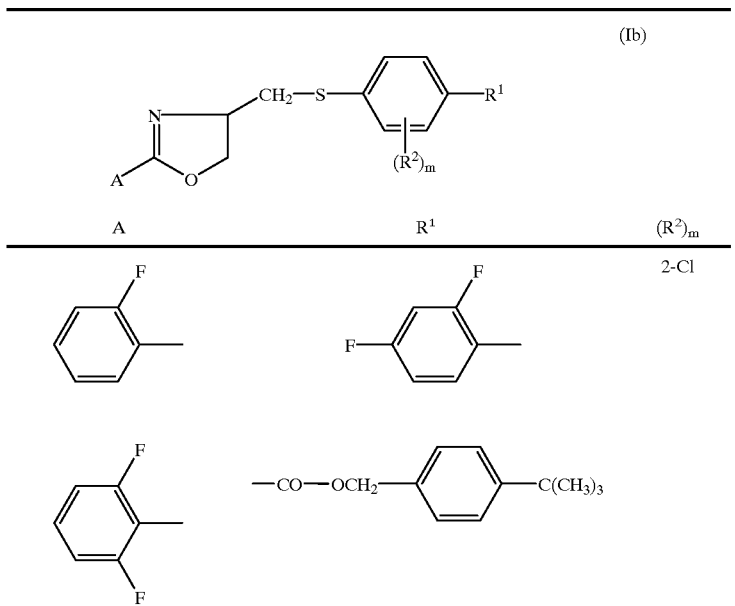

| A | R$^1$ | (R$^2$)$_m$ |
|---|---|---|
|  |  | 2-Cl |
|  |  |  |
|  | —CO—OCH$_2$—⟨Ph⟩—C(CH$_3$)$_3$ |  |

If, for example, 2-amino-3-(4-t-butylphenylthio)-1-propanol and 2,6-difluorobenzoic acid are used as starting substances and polyphosphoric acid is used as the dehydrating agent for carrying out process (a) according to the invention, the course of the reaction can be outlined by the following equation:

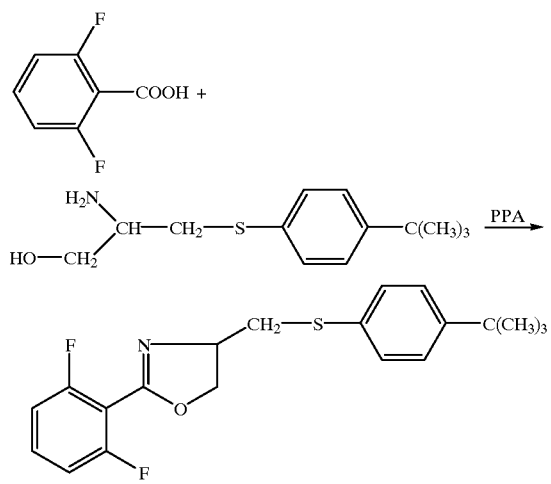

If, for example, N-[1-hydroxy-3-(4-t-butylphenylthio)-2-propyl]-2,6-difluorobenzamide is used as starting compound and phosphoric acid (PPA) as dehydrating agent for carrying out process (b) according to the invention, the course of the reaction can be outlined by the following equation:

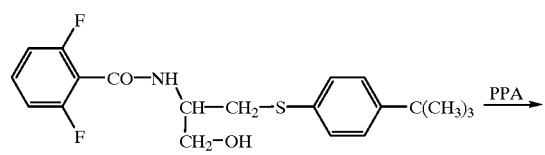

-continued

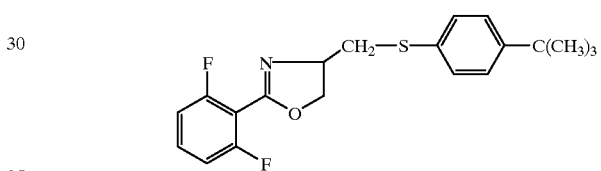

If, for example, N-[(1-chloro-3-(4-t-butylphenylthio)-2-propyl]-2,6-difluorobenzamide is used as starting compound and triethylamine as the base for carrying out process (c) according to the invention, the course of the reaction can be outlined by the following equation:

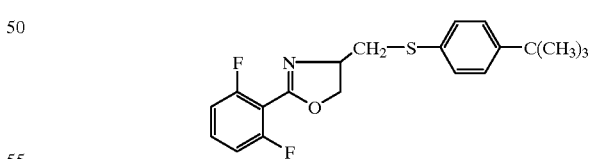

If, for example, 2-(2,6-difluorophenyl)-4-(p-tolylsulfonyloxymethyl)-1,3-oxazoline and 4-t-butyl-thiophenol are used as starting substances for carrying out process (d) according to the invention, the course of the reaction can be outlined by the following equation:

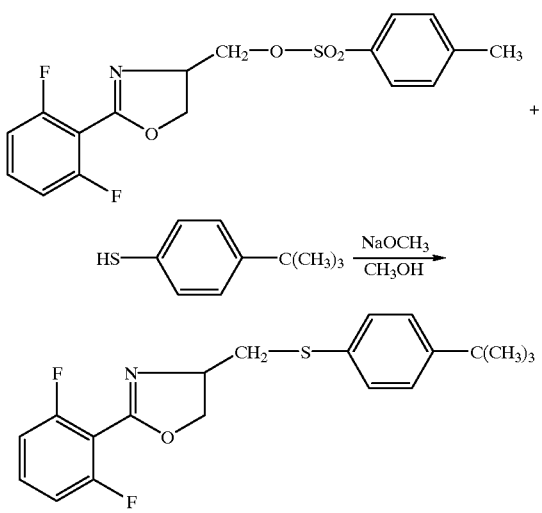

If, for example, 2-(2,6-difluorophenyl)-4-(4-t-butylphenylthiomethyl)-1,3-oxazoline is used as starting substance and hydrogen peroxide as the oxidant for carrying out process (e) according to the invention, the course of the reaction can be outlined by the following equation:

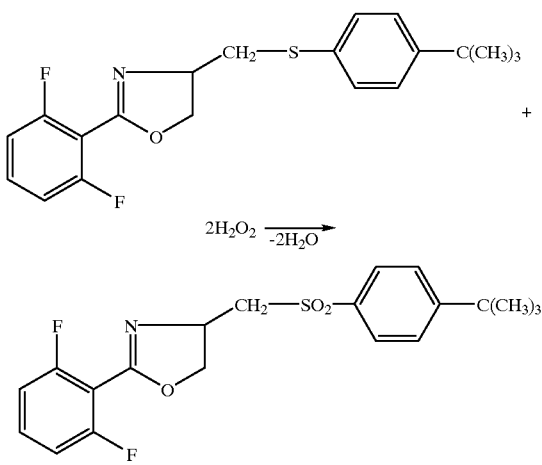

Formula (II) provides a general definition of the aminoalcohols to be used as starting substances in process (a) according to the invention for the preparation of the compounds of the formula (I). In formula (II), B and D preferably, or in particular, have the meanings which have already been mentioned above in connection with the description of the compounds of the formula (I) as being preferred, or particularly preferred for B.

The starting substances of the formula (II) are known and/or can be prepared by processes known per se by reducing the corresponding amino acids (cf., for example, Chemische Berichte 121 (1988), 2209).

Formula (III) provides a general definition of the carboxylic acids furthermore to be used as starting substances in process (a) according to the invention for the preparation of the compounds of the formula (I). In formula (III), A preferably, or in particular, has the meaning which has already been mentioned above in connection with the description of the compounds of the formula (I) as being preferred, or particularly preferred, for A. The starting substances of the formula (III) are known chemicals for organic synthesis.

Processes (a) and (b) according to the invention are carried out using a dehydrating agent. Dehydrating agents which are customary in organic chemistry can be employed. The following can preferably be used: sulfuric acid, polyphosphoric acid (PPA), phosphorus(V) oxide, dicyclohexylcarbodiimide (DCC), phosphorus(V) sulfide and the system triphenylphosphine/triethylamine/tetrachloromethane.

Suitable diluents for carrying out processes (a) to (d) according to the invention are the customary organic solvents. The following can preferably be used: aliphatic alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, tetrachloromethane; ethers, such as diethyl ether, diisopropyl ether, dioxane, tetrahydrofuran, ethylene glycol dimethyl ether or ethylene glycol ethyl ether; ketones, such as acetone, butanone or methyl isobutyl ketone; nitriles, such as acetonitrile, propionitrile or benzonitrile; amides, such as N,N-dimethylformamide and N,N-dimethylacetamide, N-methyl-pyrrolidone or hexamethylphosphoric triamide; esters such as methyl acetate or ethyl acetate, and also sulfoxides such as dimethyl sulfoxide, and, if appropriate, also alcohols such as methanol or ethanol.

When carrying out process (a) according to the invention, the reaction temperatures can be varied within a relatively substantial range. In general, the process is carried out at temperatures between 0° C. and 150° C., preferably at temperatures between 10° C. and 100° C.

In general, process (a) according to the invention is carried out under atmospheric pressure. However, it is also possible to carry out the process under elevated or reduced pressure, in general between 0.1 bar and 10 bar.

To carry out process (a) according to the invention, the starting substances required in each case are generally employed in approximately equimolar amounts. However, it is also possible to use one of the two components employed in each case in a larger excess. In general, the reactions are carried out in a suitable diluent in the presence of a dehydrating agent, and the reaction mixture is stirred for several hours at the temperature required in each case. Working-up is carried out by customary methods.

In a particular embodiment of process (a) according to the invention it is also possible to employ corresponding nitriles in place of the carboxylic acids of the formula (III), in which case a catalyst such as, for example, zinc(II) chloride, is preferably used instead of a dehydrating agent.

Formula (IV) provides a general definition of the amidoalcohols to be used as starting substances in process (b) according to the invention for the preparation of the compounds of the formula (I). In formula (IV), A, B and D preferably, or in particular, have those meanings which have already been mentioned above in connection with the description of the compounds of the formula (I) as being preferred, or particularly preferred, for A, B and D.

The starting substances of the formula (IV) are known and/or can be prepared by processes known per se (cf., for example, J. Org. Chem. 53 (1988), 1372; Tetrahedron Lett. 29 (1988), 3121).

The amidoalcohols of the formula (IV) are obtained, for example, when acid chlorides which are derived from the carboxylic acids of the formula (III) are reacted with aminoalcohols of the formula (II) at temperatures between 0° C. and 100° C. in the presence of an acid-binding agent such as, for example, triethylamine, pyridine, potassium carbonate or sodium hydroxide, and in the presence of a diluent such as, for example, toluene, chlorobenzene, acetone or acetonitrile.

The amidoalcohols of the formula (IVa)

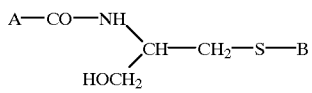

(IVa)

in which
A and B have the abovementioned meanings,
are also obtained when
ester alcohol amides of the formula (XVa)

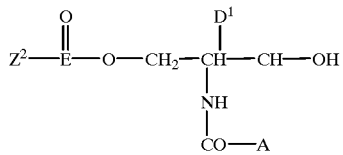

(XVa)

in which
A has the abovementioned meaning,
$Z^2$ represents alkyl or optionally substituted aryl,
E represents carbon or SO and
$D^1$ represents hydrogen,
are reacted with thiophenols of the formula (VII) in a suitable solvent such as, in particular, alcohols, in the presence of a base, such as, in particular, the corresponding alkali metal alcoholates.

When carrying out process (b) according to the invention, the reaction temperatures can be varied within a substantial range. In general, the process is carried out at temperatures between –20° C. and +150° C., preferably at temperatures between 20° C. and 140° C.

In general, process (b) according to the invention is carried out under atmospheric pressure. However, it is also possible to carry out the process under elevated or reduced pressure, in general between 0.1 bar and 10 bar.

To carry out process (b) according to the invention for the preparation of compounds of the formula (I), 1 to 20 mol, preferably 1 to 5 mol, of dehydrating agent are generally employed per mol of amidoalcohol of the formula (IV).

In a preferred embodiment of process (b) according to the invention, the amidoalcohol of the formula (IV) is introduced into a diluent, and the dehydrating agent is then metered in. The reaction mixture is stirred at the temperature required until the reaction has ended and subsequently worked up in the customary manner.

Formula (V) provides a general definition of the amide derivatives to be used as starting substances in process (c) according to the invention for the preparation of the compounds of the formula (I). In formula (V), A, B and D preferably, or in particular, have those meanings which have already been mentioned above in connection with the description of the compounds of the formula (I) as being preferred, or particularly preferred, for A, B and D; X preferably represents fluorine, chlorine, bromine, iodine, $C_1$–$C_4$-alkyl-sulfonyloxy, phenylsulfonyloxy or tolylsulfonyloxy, in particular chlorine, bromine, methylsulfonyloxy or tolylsulfonyloxy.

The starting substances of the formula (V) can be prepared by processes known per se.

The amide derivatives of the formula (V) are obtained, for example, when corresponding amidoalcohols of the formula (IV) are reacted in the customary manner with chlorinating agents such as, for example, thionyl chloride or phosphorus (V) chloride, or with sulfonylating agents such as, for example, methanesulfonyl chloride or p-toluenesulfonyl chloride, in a solvent such as, for example, methylene chloride, toluene or glacial acetic acid, in the presence or absence of a reaction accelerator such as, for example, dimethylformamide, or, in the case of the sulfonylation, a base.

Amide derivatives of the formula (Va)

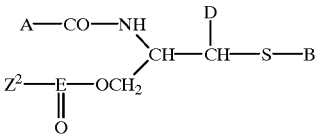

(Va)

in which

| A, D and B | have the abovementioned meanings, |
|---|---|
| E | represents carbon or SO and |
| $Z^2$ | represents alkyl or optionally substituted aryl | are obtained by reacting ester halogenoalkyl amides of the formula (XVI)

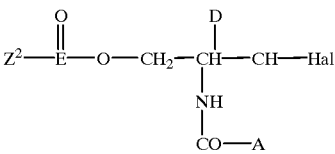

(XVI)

in which
A, D, E and $Z^2$ have the abovementioned meanings and
Hal represents chlorine, bromine or iodine, in particular chlorine or bromine,
with thiophenols of the formula (VII) in a suitable solvent such as, in particular, alcohols, in the presence of a base such as, in particular, the corresponding alkali metal alcoholates. If appropriate, the product can be cyclized further directly by means of an excess of base to give the end product of the formula (I).

Process (c) according to the invention is carried out in the presence of a base. Suitable bases are all customary inorganic or organic bases. The following can preferably be used: the hydrides, hydroxides, amides, alcoholates, acetates, carbonates or hydrogen carbonates of alkaline earth metals or alkali metals, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines such as trimethylamine, triethylamine, tributylamine, N,N-dimethylaniline, pyridine, N-methylpiperidine, N,N-dimethylaminopyridine, diazabicyclooctane (DABCO), diazabicyclonones (DBN) or diazabicycloundecene (DBU).

When carrying out process (c) according to the invention, the reaction temperatures can be varied within a substantial range. In general, the process is carried out at temperatures between −20° C. and +150° C., preferably at temperatures between 0° C. and 100° C.

In general, process (c) according to the invention is carried out under atmospheric pressure. However, it is also possible to carry out the process under elevated or reduced pressure, in general between 0.1 bar and 10 bar.

To carry out process (c) according to the invention for the preparation of the compounds of the formula (I), 1 to 3 mol, preferably 1.0 to 1.5 mol, of a base are generally employed per mol of amide derivative of the formula (V).

In a preferred embodiment of process (c) according to the invention, the amide derivative of the formula (V) is mixed with a base in a suitable diluent; the mixture is stirred at the temperature required until the reaction has ended and subsequently worked up in the customary manner.

Formula (VI) provides a general definition of the oxazolines to be used as starting substances in process (d) according to the invention for the preparation of the formula (I). In formula (VI), A and D preferably, or in particular, have those meanings which have already been mentioned above in connection with the description of the compounds of the formula (I) as being preferred, or particularly preferred, for A and D. X preferably represents halogen, $C_1$-$C_4$-alkylsulfonyloxy, phenylsulfonyloxy or tolylsulfonyloxy, in particular methylsulfonyloxy or tolylsulfonyloxy.

The starting substances of the formula (VI) are known (cf., for example, EP-A 0553623, U.S. equivalents U.S. Pat. No. 5,411,979 and U.S. Pat. No. 5,556,867) and/or can be prepared for example by the processes described in this publication.

Alternatively, they can be obtained by reacting epoxy alcohols of the formula (VIII, in which D is hydrogen or alkyl) with activated nitriles of the formula (IX) in which $Z^1$ represents an attracting radical such as, in particular, trichloromethyl, in the presence of a base, such as, for example, potassium carbonate, at 0–50° C., preferably 20–30° C., to give imino ester epoxides of the formula (X), following the general equation (e):

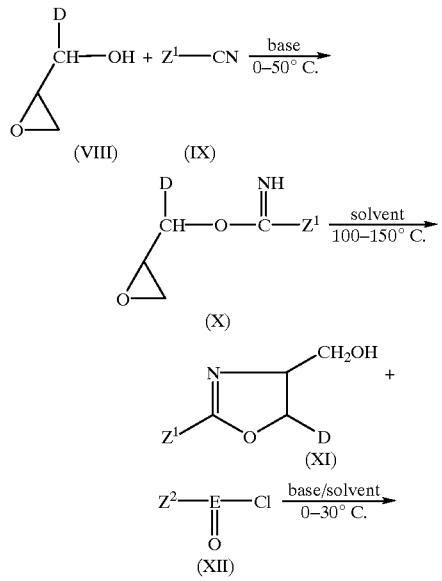

and reacting these imino ester epoxides of the formula (X) at 100–150° C. in a suitable solvent such as, for example, xylene, to give corresponding oxazolines of the formula (XI);

and these are reacted with an acid chloride of the formula (XII) in which $Z^2$ represents alkyl or optionally substituted aryl and E represents carbon or the SO group (cf. also Arch. Pharm. 322, 639 (1989)), this acylation being carried out in a suitable solvent such as, for example, ethyl acetate, at, in particular, 0–30° C., if appropriate in the presence of a base such as, for example, triethylamine.

The resulting oxazolines of the formula (XIII) can be hydrolyzed using a suitable acid, in particular an inorganic acid such as, for example, hydrochloric acid, in the presence of a solvent such as, in particular, methanol or ethanol, to give the corresponding ester alcohols of the formula (XIV);

which can be reacted with activated derivatives of the carboxylic acids of the formula (III) such as, for example, acid chlorides or acid anhydrides of the formula (IIIa; $X^1$=chlorine or A—CO—O) via a suitable acylation reaction to give ester alcohol amides of the formula (XV).

The ester alcohol amides of the formula (XV) are starting materials for the alternative process routes (f) and (g) for the preparation of oxazolines of the formulae (XVII; includes oxazolines of the formula (VI) where D=H) and (XVIII):

Process route (f):

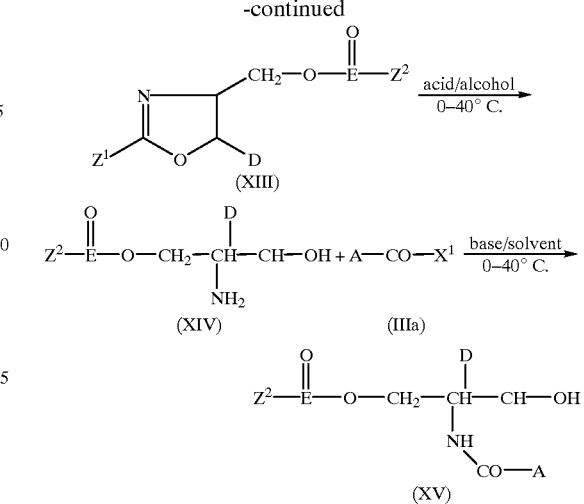

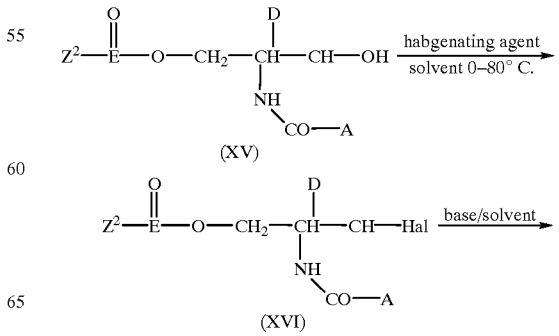

-continued

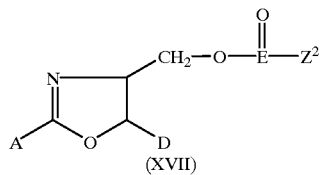
(XVII)

In process route (f), the ester alcohol amide of the formula (XV) is converted into the corresponding ester halogenoalkyl amide of the formula (XVI) using the suitable halogenating agent such as, for example, thionyl chloride, in a suitable solvent such as, for example, carbon tetrachloride, and this ester halogenoalkyl amide is cyclized to give the oxazoline of the formula (XVII), the ester group being hydrolyzed, if appropriate.

If D=H, the oxazoline of the formula (XVII) is a direct starting material for process (d) according to the invention. Process route (g):

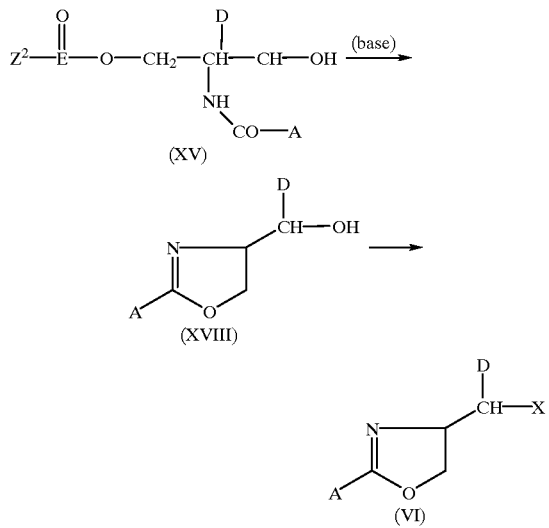

In process route (g), the ester alcohol amide of the formula (XV) is cyclized to give the oxazoline alcohol of the formula (XVIII), if appropriate in the presence of a base, and this oxazoline alcohol is reacted with sulfonyl chlorides or halogenating agents, which gives the oxazolines of the formula (VI) required for process (d) according to the invention.

Formula (VII) provides a general definition of the thiophenols furthermore to be used as starting substances in process (d) according to the invention for the preparation of the compounds of the formula (I). In formula (VII), B preferably, or in particular, has the meaning which has already been mentioned above in connection with the description of the compounds of the formula (I) as being preferred, or particularly preferred, for B.

The starting substances of the formula (VII) are known chemicals for organic synthesis.

Process (d) according to the invention is carried out in the presence of a base. Suitable bases are all customary inorganic or organic bases. The hydrides, hydroxides, amides, alcoholates, acetates, carbonates or hydrogen carbonates of alkaline earth metals or alkali metals, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclonones (DBN) or diazabicycloundecene (DBU).

When carrying out process (d) according to the invention, the reaction temperatures can be varied within a substantial range. In general, the process is carried out at temperatures between −20° C. and +150° C., preferably at temperatures between 0C and 110° C.

In general, process (d) according to the invention is carried out under atmospheric pressure. However, it is also possible to carry out the process under elevated or reduced pressure, in general between 0.1 bar and 10 bar.

To carry out process (d) according to the invention for the preparation of the compounds of the formula (I), 1 to 3 mol, preferably 1 to 1.5 mol, of thiophenol of the formula (VII) are generally employed per mol of oxazoline of the formula (VI).

In a preferred embodiment of process (d) according to the invention, the thiophenol of the formula (VII) and a base are introduced into a suitable diluent, and an oxazoline of the formula (VI) in a suitable diluent is added dropwise; the mixture is stirred at the temperature required until the reaction has ended and subsequently worked up in the customary manner.

Formula (Ia) provides a general definition of the phenylthio-oxazoline derivatives to be used as starting substances in process (e) according to the invention for the preparation of the compounds of the formula (I). In formula (Ia), A, B and D preferably, or in particular, have those meanings which have already been mentioned in connection with the description of the compounds of the formula (I) as being preferred, or particularly preferred, for A, B and D.

The starting substances of the formula (Ia) are compounds according to the invention and can be obtained in accordance with processes (a) to (d).

Suitable oxidants for carrying out process (e) according to the invention are all oxidants which can conventionally be used for sulfur oxidations. The following are preferably used: hydrogen peroxide or organic per acids such as, for example, peracetic acid, 4-nitroperbenzoic acid or 3-chloroperbenzoic acid, or else inorganic oxidants, such as per-iodic acid, potassium permanganate or chromic acid.

Suitable diluents for carrying out process (e) according to the invention are inorganic or organic solvents, depending on the oxidant used. The following are preferably used: alcohols, such as methanol or ethanol, or their mixtures with water, and also pure water, acids or acid anhydrides such as, for example, acetic acid, acetic anhydride or propionic acid or dipolar aprotic solvents, such as acetonitrile, acetone, ethyl acetate or dimethylformamide, and also optionally halogenated hydrocarbons such as benzine, benzene, toluene, hexane, cyclohexane, petroleum ether, dichloromethane, dichloroethane, chloroform, carbon tetrachloride or chlorobenzene.

If appropriate, process (e) according to the invention can be carried out in the presence of a reaction auxiliary. Suitable reaction auxiliaries are all organic and inorganic acid-binding agents which can be conventionally used. The following are preferably used: the hydroxides, acetates or carbonates of alkaline earth metals or alkali metals, such as, for example, calcium hydroxide, sodium hydroxide, sodium acetate or sodium carbonate.

If appropriate, process (e) according to the invention can be carried out in the presence of a suitable catalyst. Suitable catalysts are all those which can conventionally be used for such sulfur oxidations. Heavy-metal catalysts are preferably used; ammonium molybdate and sodium tungstate may be mentioned in this context by way of example.

When carrying out process (e) according to the invention, the reaction temperatures can be varied within a substantial range. In general, the process is carried out at temperatures between −30° C. and +100° C., preferably at temperatures between 0° C. and 80° C.

In general, process (e) according to the invention is carried out under atmospheric pressure. However, it is also possible to carry out the process under elevated or reduced pressure.

To carry out process (e) according to the invention, 0.8 to 1.2 mol, preferably equimolar amounts, of oxidant are generally employed per mol of phenylthio-oxazoline derivative of the formula (Ia) if it is desired to interrupt the oxidation of the sulfur at the sulfoxide level. For an oxidation to the sulfone, 1.8 to 3.0 mol. preferably twice the molar amount, of oxidant are generally employed per mol of phenylthio-oxazoline derivative of the formula (Ia). The reaction is carried out and the end products of the formula (I) are worked up and isolated by customary processes.

The active compounds are suitable for combating animal pests, preferably arthropods and nematodes, in particular insects and arachnids, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Euryga ster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastro-philus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

At suitable application rates, the compounds according to the invention also show a fungicidal activity.

The active compounds can be converted to the customary formulations, such as solutions, emulsions, wettable powders, suspensions, powders, dusts, pastes, soluble powders, granules, suspoemulsion concentrates, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dye-stuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms, and the like.

The following compounds may be mentioned:
acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambda-cyhalothrin, permethrin, pyresmethrin, pyrethrum, silafluofen, tralomethrin, zetamethrin, alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion phorate, malathion, mecarbam, mevinphos, mesulfenphos, methacrifos, methamidophos, naled, omethoate, oxydemeton M, oxydeprofos, parathion A, parathion M, phenthoate, phorate, phosalone, phosmet, phosphamidon, phoxim, pirimiphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumuron, imidacloprid, nitenpyram, N-[(6-chloro-3-pyridinyl)-methyl]-N'-cyano-N-methylethaneimideamide (NI-25), abamectin, amitrazin, avermectin, azadirachtin, bensultap, Bacillus thuringiensis, cyromazine, diafenthiuron, emamectin, ethofenprox, fenpyrad, fipronil, flufenprox, lufenuron, metaldehyd, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimdiphos, tefluthrin, terbufos, thiodicarb, thiafenox, azocyclotin, butylpyridaben, clofentezine, cyhexatin, diafenthiuron, diethion, emamectin, fenazaquin, fenbutatin oxide, fenothiocarb, fenpropathrin, fenpyrad, fenpyroximate, fluazinam, fluazuron, flucycloxuron, flufenoxuron, fluvalinate, fubfenprox, hexythiazox, ivemectin, methidathion, monocrotophos, moxidectin, naled, phosalone, profenofos, pyraclofos, pyridaben, pyrimidifen, tebufenpyrad, thuringiensin, triarathene and 4-bromo-2-(4-chlorophenyl)-1-(ethoxymethyl)-5-(trifluoromethyl)-1H-pyrrole-3-carbonitrile (AC 303630).

The active compounds according to -the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compounds according to the invention are not only active against plant, hygiene and stored product pests, but also, in the veterinary medicine sector, against animal parasites (ectoparasites and endoparasites), such as scaly ticks, Argasidae, scab mites, Trombidae, flies (stinging and sucking), parasitic fly larvae, lice, hair lice, bird lice, fleas, and endoparasitic worms. For example, they show an outstanding activity against ticks such as, for example, *Boophilus microplus*.

The active compounds of the formula (I) according to the invention are also suitable for combating arthropods which attack agricultural livestock such as, for example, cattle, sheep, goats, horses, pigs, donkeys, camels, buffalo, rabbits, chickens, turkeys, ducks, geese, honeybees, other domestic animals such as, for example, dogs, cats, cage birds, aquarium fish and so-called laboratory animals such as, for example, hamsters, guinea pigs, rats and mice. By combating these arthropods, it is intended to reduce death and reduce performance (in the case of meat, milk, wool, hides, eggs, honey or the like), so that more economical and simpler animal keeping is possible by applying the active compounds according to the invention.

The application of the active compounds according to the invention is effected in the veterinary sector in a known fashion, by enteral administration in the form of, for example, tablets, capsules, potions, drenches, granules, pastes, boli, by the feed-through method, and in the form of suppositories, by parenteral administration such as, for example, by injections (intramuscular, subcutaneous, intravenous, intraperitonal and the like), implants, by nasal application, by dermal application, for example in the form of immersing or dipping, spraying, pouring-on and spotting-on, washing, dusting, and with the aid of shaped articles containing active compound, such as collars, ear tags, tail tags, limb bands, halters, marking devices and the like.

Preparation and use of the substances according to the invention are illustrated with the aid of the examples which follow:

PREPARATION EXAMPLES

Example 1

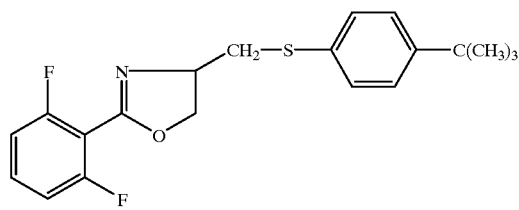

(Process d)

0.3 g (6 mmol) of sodium methylate is added to 1 g (6 mmol) of 4-t-butyl-thiophenol in 50 ml of methanol (slightly exothermic). 2.1 g (6 mmol) of 2-(2,6-difluorophenyl)-4-(p-tolylsulfonyloxymethyl)-1,3-oxazoline in 30 ml of methanol are added dropwise to this solution at 40° C. The reaction mixture is stirred for 2 hours at 40° C. and then for 16 hours under reflux. The solvent is then distilled off, the residue is taken up in 100 ml of ethyl acetate, and the mixture is washed three times using in each case 50 ml of water. The solvent is stripped off, and the residue is chromatographed by silica gel column chromatography using toluene:ethyl acetate 10:1 as the eluent.

0.9 g (41.6% of theory) of 2-(2,6-difluorophenyl)-4-(4-t-butylphenylthiomethyl)-1,3-oxazoline of partition coefficient log P (octanol/water) of approximately 4.64 and a refractive index $n_D^{20}$=1.5660 is obtained.

The compounds of the formula (I) listed below can be obtained analogously to Example 1 and in accordance with the general information on the preparation

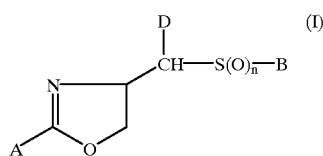

| Ex. No. | A | D | n | B | physical constants |
|---|---|---|---|---|---|
| 2 | 2,6-difluorophenyl | H | O | 3-CF$_3$-phenyl | $n_D^{20}$ = 1.5433 |
| 3 | 2,6-difluorophenyl | H | O | 4-Cl-2-CF$_3$-phenyl | m.p.: 89–90° C. |

-continued

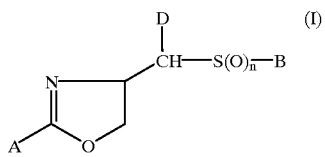

| Ex. No. | A | D | n | B | physical constants |
|---|---|---|---|---|---|
| 4 | 2,6-difluorophenyl | H | O | 2,3-dichloro-4-(trifluoromethyl)phenyl... | m.p.: 153–155° C. |
| 5 | 2,6-difluorophenyl | H | O | pentachlorophenyl | m.p.: 130° C. |
| 6 | 2,6-difluorophenyl | H | O | 4-(4-methylbenzoyl)phenyl | $n_D^{20} = 1.6313$ |
| 7 | 2,6-difluorophenyl | H | O | 3,5-dichloro-4-(trifluoromethyl)phenyl | m.p.: 80–82° C. |
| 8 | 2,6-difluorophenyl | H | O | 4-methoxyphenyl | $n_D^{20} = 1.5843$ |
| 9 | 2,6-difluorophenyl | H | O | 4-acetyl-2-chlorophenyl | m.p.: 69–73° C. |
| 10 | 2,6-difluorophenyl | H | O | 4-chlorophenyl | $n_D^{20} = 1.5943$ |

-continued $$\underset{A}{\overset{N}{\bigcirc}}\overset{D}{\underset{\text{CH}-\text{S(O)}_n-B}{\bigg|}} \quad (I)$$

| Ex. No. | A | D | n | B | physical constants |
|---|---|---|---|---|---|
| 11 | 2-F-phenyl | H | 0 | 4-Cl-phenyl | m.p.: 56° C. |
| 12 | 2-F-phenyl | H | 0 | 4-C₄H₉t-phenyl | $n_D^{20}$ = 1,5804 |
| 13 | 2-F-phenyl | H | 0 | 3-CF₃-4-Cl-phenyl | m.p.: 72° C. |
| 14 | 2,6-di-F-phenyl | H | 0 | 3-Cl-phenyl | $n_D^{20}$ = 1.5926 |
| 15 | 2,6-di-F-phenyl | H | 0 | 3-CF₃-4-CN-phenyl | GC MS spectrum<br>Mol. peak: 398<br>Main peaks: 182, 154, 127<br>Sec. peaks: 379, 351, 326, 309, 240, 216, 196<br>Ret. index: 2479 |
| 16 | 2,6-di-F-phenyl | H | 0 | 3-CF₃-4-CO₂CH₃-phenyl | GC MS spectrum<br>Mol. peak: 431<br>Main peaks: 182, 154, 127<br>Sec. peaks: 412, 400, 384, 342, 250, 219, 204, 196<br>Ret. index: 2639 |
| 17 | 2,6-di-F-phenyl | H | 0 | 3-CH₃-4-C(O)OSi(CH₃)₃-phenyl | GC MS spectrum<br>Mol. peak: 435<br>Main peaks: 182, 196, 154, 141, 127<br>Sec. peaks: 420, 388, 363, 346, 317, 278, 254, 239<br>Ret. index: 2936 |
| 18 | 2,6-di-F-phenyl | H | 0 | 3-CH₃-4-C(O)OC(CH₃)₃-phenyl | GC MS spectrum<br>Mol. peak: 419<br>Main peaks: 182, 196, 154, 141, 127<br>Sec. peaks: 386, 372, 346, 262, 223<br>Ret. index: 3095 |

-continued
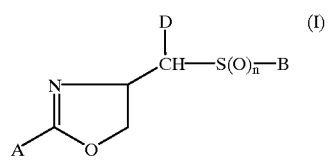
| Ex. No. | A | D | n | B | physical constants |
|---|---|---|---|---|---|
| 19 | 2,6-difluorophenyl | H | 0 | 2,4,5-trichlorophenyl | m.p.: 83° C. |
| 20 | 2,6-difluorophenyl | H | 0 | 2-nitro-4-chlorophenyl | m.p.: 117° C. |
| 21 | 2,6-difluorophenyl | H | 0 | 4-(CO—O—CH(CH₃)₂)phenyl | log P 3.93 (octanol/H₂O) |
| 22 | 2,6-difluorophenyl | H | 0 | 2,6-dichlorophenyl | m.p.: 134° C. |
| 23 | 2,6-difluorophenyl | H | 0 | 2,4-dichlorophenyl | m.p.: 63° C. |
| 24 | 2,6-difluorophenyl | H | 0 | 3-bromophenyl | m.p.: 63° C. |

Preparation of the starting compound

Example (VI-1)

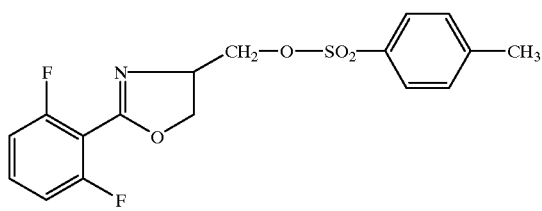

5.6 ml (0.069 mol) of pyridine are added to 5.3 g (0.023 mol) of 2-(2,6-difluorophenyl)-4-hydroxymethyl-1,3-oxazoline in 100 ml of ethyl acetate, and 4.4 g (0.023 mol) of p-toluenesulfonyl chloride in 50 ml of ethyl acetate are subsequently added dropwise. During this process, the temperature climbs to 50° C. Stirring is continued for 2.5 hours at 50° C. and subsequently for 8 hours under reflux conditions. The organic phase is washed four times using in each case 50 ml of water, and the solvent is distilled off. The residue is chromatographed by silica gel column chromatography using an eluent gradient of toluene and ethyl acetate.

2.1 g (24.8% of theory) of 2-(2,6-difluorophenyl)-4-(p-t-olylsulfonyloxymethyl)-1,3-oxazoline of partition coefficient log P (octanol/water) of approximately 2.68 and a refractive index $n_D^{20}=1.5491$ are obtained.

Example (XVIII-1)

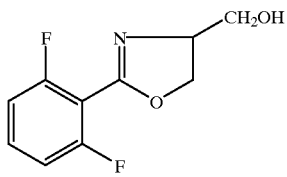

6.5 g (0.0168 mol) of N-[1-chloro-3-(4-t-butylbenzoyloxy)-2-propyl]-2,6-difluorobenzamide are dissolved in 100 ml of methanol. 2 ml (0.033 mol) of 45% strength sodium hydroxide solution are added, and the mixture is stirred for 4 hours under reflux. After the solvent has been distilled off, the residue is taken up in 100 ml of ethyl acetate, the mixture is washed three times using in each case 50 ml of water, and the solvent is distilled off.

2.8 g (72% of theory) of 2-(2,6-difluorophenyl)-4-hydroxymethyl-1,3-oxazoline of melting point 82° C. are obtained.

Example (XVI-1)

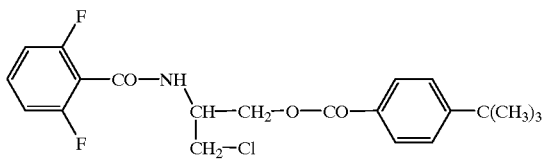

9 g (0.023 mol) of N-[1-hydroxy-3-(4-t-butylbenzoyloxy)-2-propyl]-2,6-difluorobenzamide are suspended in 60 ml of carbon tetrachloride, 1.7 ml (0.023 mol) of thionyl chloride are added, and the mixture is refluxed for 1.5 hours. The solvent is distilled off.

9.3 g of N-[1-chloro-3-(4-t-butylbenzoyloxy)-2-propyl]-2,6-difluorobenzamide having a partition coefficient log P (octanol/water) of approximately 3.86 are obtained.

Example (XV-1)

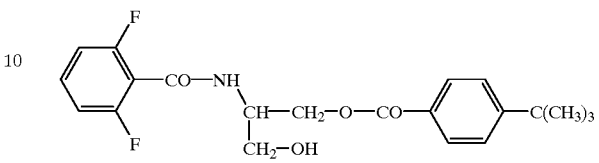

21.9 ml (0.158 mol) of triethylamine are first added to 21 g of 2-amino-3-(4-t-butylbenzoyloxy)-1-propanol hydrochloride in 400 ml of ethyl acetate, and 13.9 g of 2,6-difluorobenzoyl chloride in 20 ml of ethyl acetate are subsequently added dropwise at 0° C. Stirring is continued for 1 hour at 20° C.; the precipitate is filtered off with suction, the organic phase is washed three times using in each case 100 ml of water, the solvent is distilled off and the residue is stirred with diisopropyl ether.

After drying, 14 g (48% of theory) of N-[1-hydroxy-3-(4-t-butylbenzoyloxy)-2-propyl]-2,6-difluorobenzamide having a partition coefficient log P (octanol/water) of 2.82 are obtained.

Example A

Tetranychus test (OP resistant)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with emulsifier-containing water to the desired concentration.

Bean plants (*Phaseolus vulgaris*) which are severely infested with all development stages of the greenhouse red spider mite (*Tetranychus urticae*) are sprayed with a preparation of active compound of the desired concentration.

After the desired period of time, the effectiveness in % is determined. 100% means that all the spider mites have been killed; 0% means that none of the spider mites have been killed.

In this test, a destruction of 98% was caused, after 7 days, for example by the compounds of Preparation Examples 2 and 3 at an exemplary active compound concentration of 0.01%.

Example B

Phaedon larvae test

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), while the leaves are still moist.

After the desired period of time, the destruction in % is determined. 100% means that all the beetle larvae have been killed; 0% means that none of the beetle larvae have been killed.

In this test, a degree of destruction of 100% is shown, after 7 days, for example by the compound of Preparation Example 1 at an active compound concentration of 0.1%.

Example C

Plutella test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the desired period of time, the destruction in % is determined. 100% means that all the caterpillars have been killed; 0% means that none of the caterpillars have been killed.

In this test, a destruction of 100% was caused, after 7 days, for example by the compound of Preparation Example 2 at an exemplary active compound concentration of 0.1%.

Example D

Nephotettix test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with larvae of the green rice leafhopper (*Nephotettix cincticeps*) while the leaves are still moist.

After the desired period of time, the destruction in % is determined. 100% means that all the leafhoppers have been killed; 0% means that none of the leafhoppers have been killed.

In this test, a destruction of 100% was caused, after 6 days, for example by the compounds of Preparation Examples 2, 7 and 8 at an exemplary active compound concentration of 0.1%.

Patent claims:

1. A phenylthio-oxazoline compound of the formula (I)

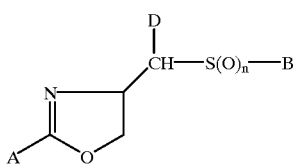

(I)

in which

A represents

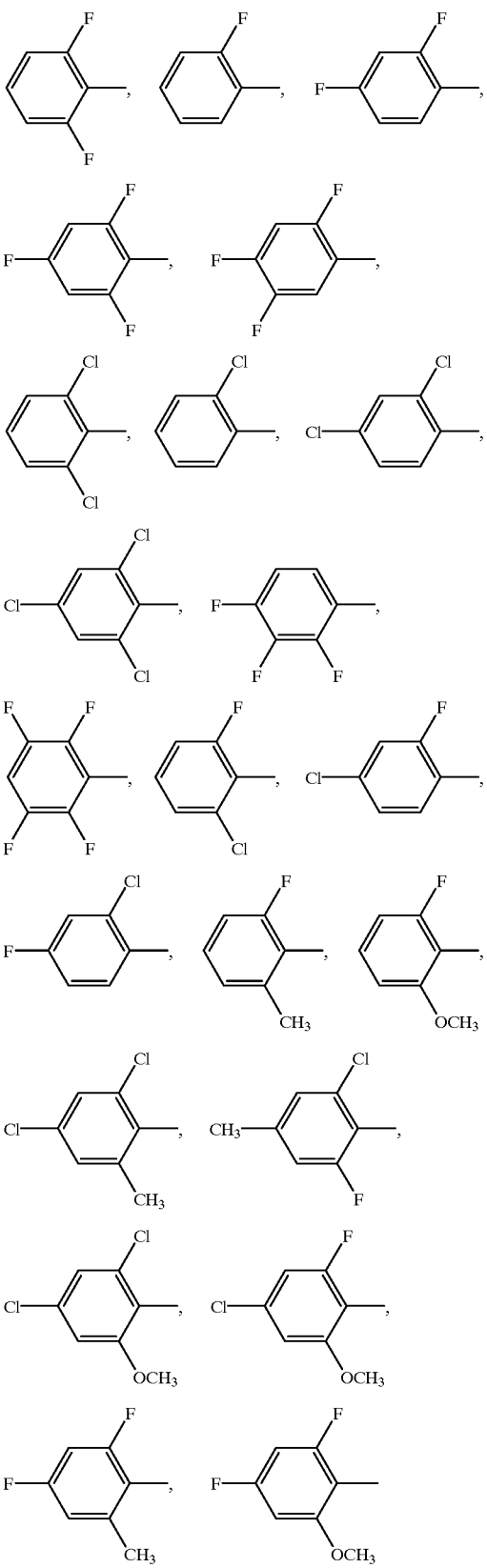

and

B represents
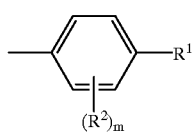
wherein R¹ represents
| R¹ |
|---|
| Cl |
| F |
| —C$_4$H$_9$-t |
| —C$_6$H$_{13}$-n |
| —C$_{12}$H$_{25}$-n |
| —C$_{10}$H$_{21}$-n |
| —C$_8$H$_{17}$-n |
| —C$_9$H$_{19}$-n |
| CF$_3$ |
| —CF$_2$CHF$_2$ |
| —OC$_6$H$_{13}$-n |
| —OC$_8$H$_{17}$-n |
| —OC$_{12}$H$_{25}$-n |
| —OCF$_3$ |
| —OCF$_2$CHF$_2$ |
| —OCH$_2$CF$_3$ |
| —OCF$_2$CHFCH$_3$ |
| —CO—C$_4$H$_9$-i |
| —OCF$_2$CHFCF$_3$ |
| —CH$_2$CH$_2$—O—C$_2$H$_5$ |
| —CH$_2$CH$_2$—O—C$_4$H$_9$-n |
| —CH$_2$CH$_2$—O—C$_6$H$_{13}$-n |
| 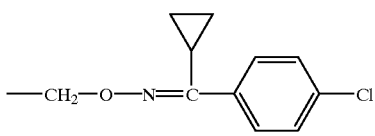 |
| —SC$_4$H$_9$-n |
| —SC$_6$H$_{13}$-n |
| —SC$_8$H$_{17}$-n |
| —SC$_{12}$H$_{25}$-n |
| —SCF$_3$ |
| —SCF$_2$CHF$_2$ |
| —SCF$_2$CHFCH$_3$ |
| —CO—CH$_3$ |
|  |
| 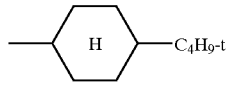 |
| 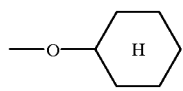 |
|  |
-continued
| R₁ |
|---|
| 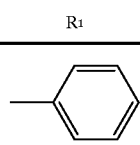 |
|  |
| 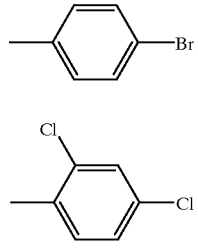 |
| 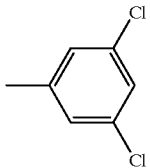 |
| 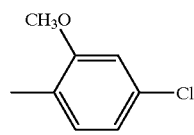 |
| 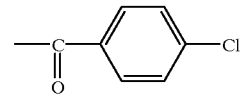 |
| 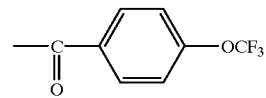 |
| 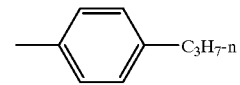 |
| 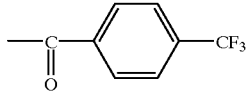 |
| 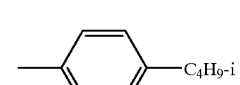 |
| 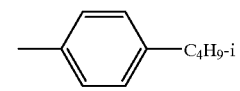 |

-continued
| R1 |
|---|
| 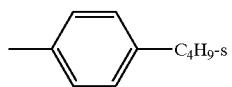 |
| 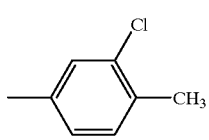 |
| 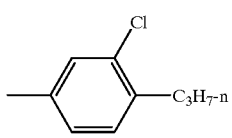 |
| 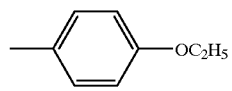 |
| 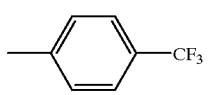 |
| 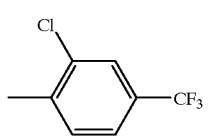 |
| 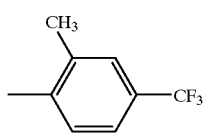 |
| 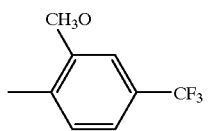 |
| 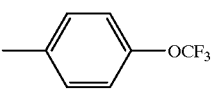 |
| 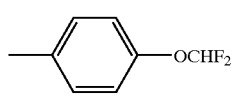 |
| 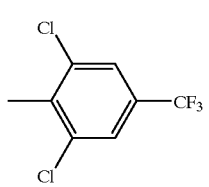 |
-continued
| R¹ |
|---|
| 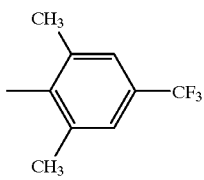 |
| 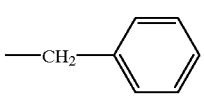 |
| 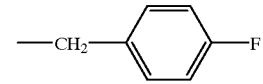 |
| 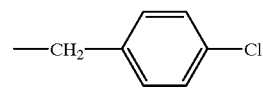 |
| 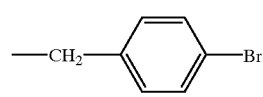 |
| 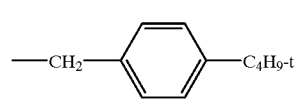 |
| 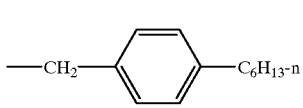 |
| 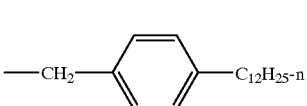 |
| 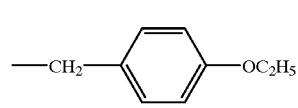 |
| 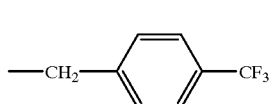 |
| 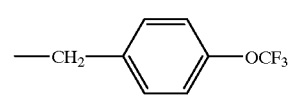 |
| 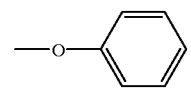 |
| 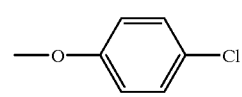 |

-continued
R¹
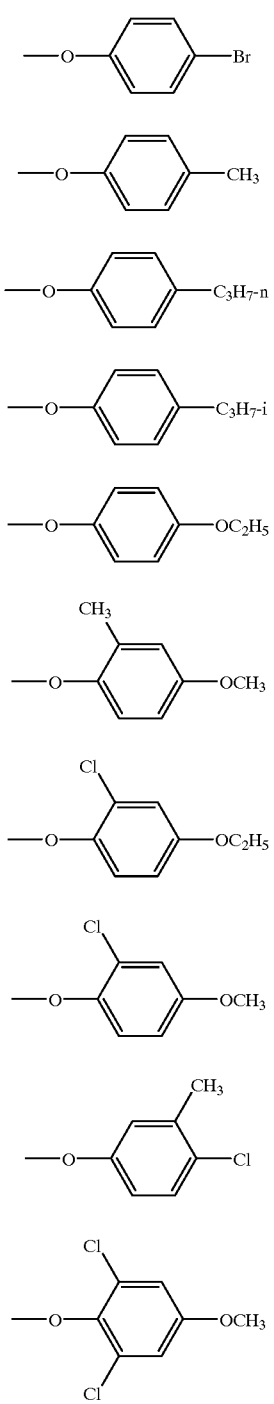
-continued
R¹
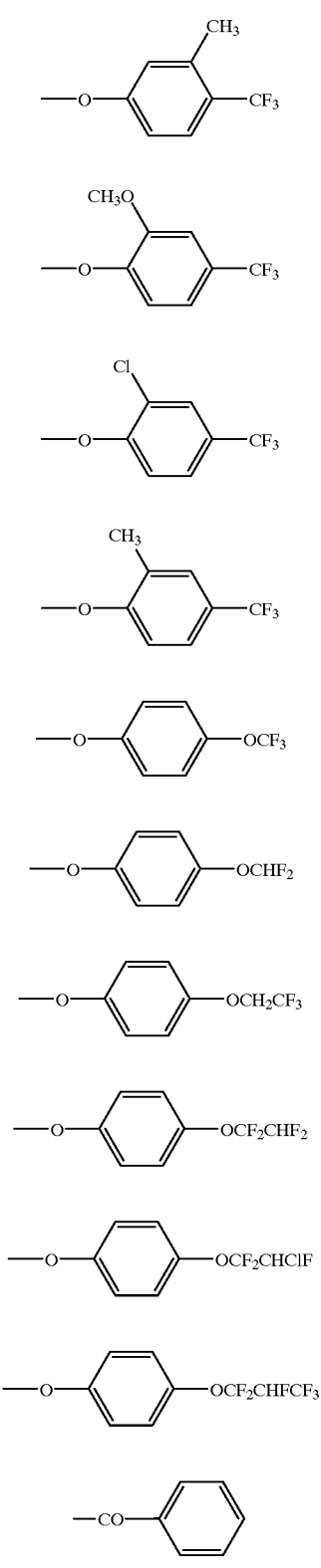

-continued
R¹
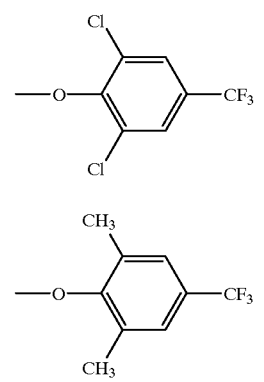
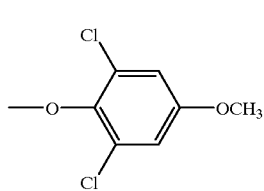
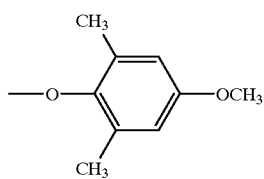
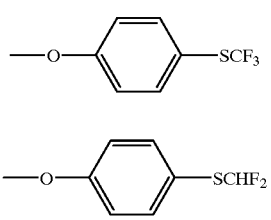
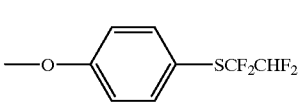
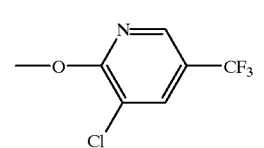
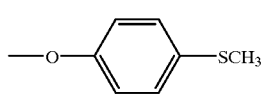
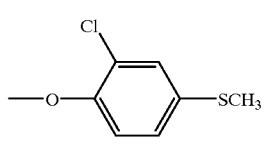
-continued
R¹
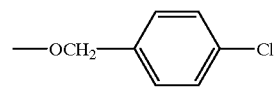
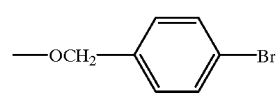
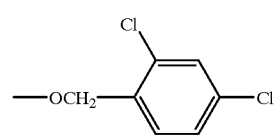
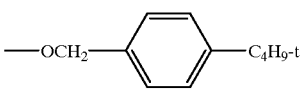
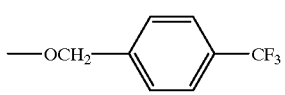
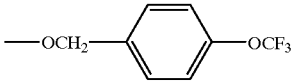
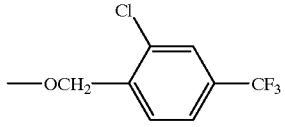
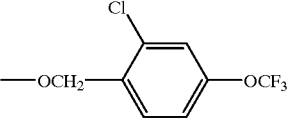
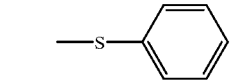
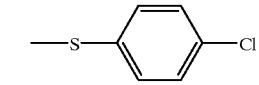
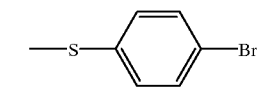
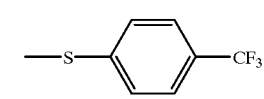
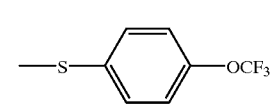

-continued

| $R^1$ |
|---|
| H | and
$R^2)_m$ represents

| $(R^2)_m$ |
|---|
| —CO—O—$C_4H_9$-t |
| —CN |
| H |
| 2-Cl |
| 2-F |
| 3-Cl |
| 2,6-$Cl_2$ |
| 3,5-$Cl_2$ |
| 3,5-$F_2$ |
| 2,5-$Cl_2$ |
| 3,5-$Cl_2$; 2-F |
| 2,3-$F_2$ |
| 2,5-$F_2$ |
| 2,3,5,6-$Cl_4$ |
| 3-$CF_3$ |
| —CO—NH—$C_4H_9$-t |
| 2-$CH_3$ |
| 2-$OCH_3$ |
| 2-$Cl_2$ |
| 2,6-$OC_2H_5$ |
| 3-$CH_3$ |
| 3,5-$OCH_3$ |
| 3-$OC_6H_5$ |
| together with $R^1$ represents |
| 3,4-$OCF_2O$— |
| 3,4-$OCF_2CF_2O$ |
| 2-Cl; 3-$CF_3$ |
| 2-Cl; 5-$CF_3$ |

D represents hydrogen or methyl and
n represents 0, 1 or 2.

2. A phenylthio-oxazoline compound of the formula

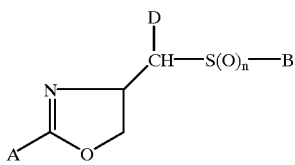

(I)

in which
A represents phenyl which is monosubstituted to disubstituted by identical or different substituents selected from the group consisting of F, Cl, and Br;

B represents phenyl and biphenyl which is optionally mono substituted to trisubstituted by identical or different substituents selected from the group consisting of F, Cl, Br, $C_1$–$C_4$-alkyl, and $C_1$–$C_4$-alkoxy which is monosubstituted to hexasubstituted by identical or different substituents selected from the group consisting of F and Cl, and $C_1$–$C_2$-alkyl which is monosubstituted to pentasubstituted by identical or different substituents selected from the group consisting of F and/or Cl, D represents hydrogen and n represents 0.

3. A pesticide which comprises a pesticidally effective amount of at least one compound of the formula (I) as claimed in claim 2 and a diluent.

4. A method of killing insects, arachnida and nematodes, which comprises allowing an effective amount of at least one compound of the formula (I) as claimed in claim 2 to act on said insects, arachnida and nematodes and/or their environment.

5. A phenylthio-oxazoline compound according to claim 2, wherein A is phenyl monosubstituted F, Cl, or Br.

6. A pesticide which comprises a pesticidally effective amount of at least one compound of the formula (I) as claimed in claim 2.

7. A method for combating insects, arachnids and nematodes which comprises allowing an effective amount of at least one compound of the formula (I) as claimed in claim 2 to act on said insects, arachnids and nematodes and/or their environment.

8. A phenylthio-oxazoline compound according to claim 2 in which

A represents phenyl which is monosubstituted to disubstituted by identical or different substituents selected from the group consisting of F, Cl, and Br, B represents phenyl and biphenyl which is optionally monosubstituted to trisubstituted by identical or different substituents selected from the group consisting of $C_1$–$C_4$-alkyl and $C_1$–$C_4$-alkoxy which is monosubstituted to hexasubstituted by identical or different substituents selected from the group consisting of F and Cl, D represents hydrogen and n represents 0.

9. A phenylthio-oxazoline compound according to claim 2, in which A represents 2,6-difluorophenyl, n is 0, D is H, and B represents phenyl monosubstituted with methoxy.

10. A phenylthio-oxazoline compound according to claim 2, in which A represents 2,6-difluorophenyl, n is 0, D is H, and B represents phenyl monosubstituted with t-butyl.

11. A phenylthio-oxazoline compound according to claim 2, in which A represents 2,6-difluorophenyl, n is 0, D is H, and B represents phenyl monosubstituted with trifluoromethoxy substituted phenyl.

* * * * *